United States Patent [19]

Khosla et al.

[11] Patent Number: 5,521,077
[45] Date of Patent: May 28, 1996

[54] METHOD OF GENERATING MULTIPLE PROTEIN VARIANTS AND POPULATIONS OF PROTEIN VARIANTS PREPARED THEREBY

[75] Inventors: Chaitan Khosla; Robert Caren, both of Stanford, Calif.

[73] Assignee: The Leland Stanford Junior University, Palo Alto, Calif.

[21] Appl. No.: 234,023

[22] Filed: Apr. 28, 1994

[51] Int. Cl.⁶ .................................................. C12N 15/00
[52] U.S. Cl. ...................... 435/172.3; 435/252.3; 435/252.33
[58] Field of Search ............................ 435/172.3, 252.3, 435/252.33

[56] References Cited

PUBLICATIONS

Burton, Dennis R. (1993) "Monoclonal antibodies from combinatorial libraries" *Acc. Chem. Res.* 26:405–411.
Clackson et al., "Making antibody fragments using phage display libraries" (1991) *Nature* 352:624–628.
Cormack, B. P., et al. (1993) "Regional codon randomization: Defining a TATA–binding protein surface required for RNA polymerase III transcription" *Science* 262:244–248.
Cwirla et al., (1990) "Peptides on phage: A vast library of peptides for identifying ligands" *PNAS* 87:6378–6382.
Delagrave, S., et al. (1993) "Searching sequence space to engineer proteins: Exponential ensemble mutagenesis" *Bio/Technology* 11:1548–1552.
Gram, H., et al. (1992) "In vitro selection and affinity maturation of antibodies from a naive combinatorial immunoglobulin library" *PNAS USA* 89:3576–3580.
Huse et al., (1989) "Generation of large combinatorial library of the immunoglobin repertoire in phage lambda" *Science* 246:1275–1289.
Lehman et al., (1993) "Evolution in vitro of an RNA enzyme with altered metal dependence" *Nature* 361:182–184.
Lowman et al., (1991) "Selecting high affinity binding proteins by monovalent phage display" *Biochemistry* 30:10832–10838.
Mullinax et al. (1990) "Identification of human antibody fragment clones specific for tetanus toxoid in a bacteriophage λ immunoexpression library", *PNAS USA* 87:8095–8099.
Sassanfar et al., (1993) "An RNA motif that binds ATP" *Nature* 364:550–553.
Waterhouse, P., et al. (1993) "Combinatorial infection and in vivo recombination: A strategy for making large phage antibody repertoires" *Nucleic Acids Research* 21:2265–2266.
Wells, J. A., (1992) "Rapid evolution of peptide and protein binding properties in vitro" *Curr. Opin. Struct. Biol.* 2:597–604.

*Primary Examiner*—James Martinell
*Attorney, Agent, or Firm*—Reed & Robins

[57] ABSTRACT

A method based on generalized recombination is provided for generating multiple protein variants. The method involves introducing into host cells at least two pools of mutant encoding nucleotide sequences, recipient and donor, transducing the donor pool into the recipient cells and subsequently screening and selecting the recombinants thereby produced for expressed proteins exhibiting desired characteristics. A population of such protein variants is also provided.

26 Claims, 3 Drawing Sheets

METHOD OF GENERATING MULTIPLE PROTEIN VARIANTS AND POPULATIONS OF PROTEIN VARIANTS PREPARED THEREBY

TECHNICAL FIELD

The present invention relates generally to methods of generating random protein variants. In particular, the invention pertains to methods whereby pools of mutant encoding nucleotide sequences are amplified, infected, transduced and screened to produce large populations of random protein variants.

BACKGROUND

Recombinant DNA technology has become a tool for studying the relationship between protein structure and function. In particular, properties of a given protein can be changed by engineering mutations in the gene encoding the protein. Recently, there has been renewed interest in the practice of screening and selecting among random mutants for structurally altered proteins with properties of interest (Wells et al. (1992) *Curr. Opin. Struct. Biol.* 2:597–604; Gram et al. (1992) *Proc. Natl. Acad. Sci. USA* 89:3576–3580; Delagrave et al. (1993) *Bio/Technology* 11:1548–1552).

It has become possible to construct large pools of random mutants which encompass virtually every possible single mutant of a given protein using modern techniques of molecular biology. For example, there are 9,500 different single mutants of a 500 amino acid protein; using recombinant DNA methods, one can generate a population of 75,000 independent clones which includes every possible single mutant (Cormack et al. (1993) *Science* 262:244–248). However, due to limits in transformation technologies, which typically yield $10^7$ transformants per experiment, it is only possible to sample a very small fraction of all possible double mutants without resorting to intermediate selection steps. (A protein of 500 amino acids has on the order of $10^8$ possible double mutants.)

A potential exception to this is exemplified by the work of Winter and coworkers (Waterhouse et al. (1993) *Nucleic Acids Research* 21:2265–2266), who utilized an in vivo site-specific recombination system to combine light chain antibody genes with heavy chain antibody genes for expression in a phage display system. Theoretically, this strategy could be used to generate a library of as many as $10^{14}$ ($10^7 \times 10^7$) $F_{AB}$ (or phab) expressing clones.

The general technique for identifying protein variants with desired characteristics, as summarized in Delagrave et al., supra, involves exhaustively sampling all possible single mutants of a target protein for any property of interest. (This strategy can be modified to incorporate a small subset of double mutants.) Candidate mutations that emerge from such screens are then combinatorially assembled into ensembles of multiple mutants, which can be iteratively screened for further improvement in the property of interest.

In many applications, however, a sufficiently sensitive method to screen more than $10^7$ mutants in a single step is unavailable. For example, in situations where screening involves affinity "panning", the isolation of a desirable mutant is limited by the resolution of a chromatography column. It is by no means clear that the mere availability of a mutant library containing more than $10^7$ clones would result in the isolation of a superior mutant in a single step. In such situations an iterative mutagenesis and screening strategy, which gradually converges to an acceptable solution in sequence space, may be unavoidable.

Disclosure

In order to address the above-described deficiencies in the art, the inventors herein disclose a novel method (called "recombination-enhanced mutagenesis") for in vivo mutant construction that can exceed the limitation of $10^7$ mutant proteins by several orders of magnitude, thereby facilitating a more exhaustive search of protein sequence space for useful double and possibly even triple mutants. Since this method does not require the introduction of a specific recombination site, it can be used to randomly recombine multiple mutations whose relative positions in the wild-type encoding nucleotide sequence are unknown.

Using recombination-enhanced mutagenesis it is possible to generate arbitrarily large libraries of multiple mutants in a protein of interest. Therefore, given a sufficiently "clean" screening/selection technique, such as in vivo selection of a metabolically essential protein, it is be possible to sample virtually all possible double (and even triple) mutants in a single selection step.

Recombination-enhanced mutagenesis also eliminates the need for iterative mutagenesis and cloning. This is possible because, after a first round of "panning," the enriched mutant pool can be recombined with the initial mutant pool to generate a second generation mutant pool. In other words, only one high quality mutant pool needs to be constructed via in vitro mutagenesis.

Accordingly, in one embodiment, the invention is directed to a method of generating multiple protein variants. The method comprises:

a) providing first and second sets of allelic mutants, wherein said first set of allelic mutants comprises at least one recipient pool of mutant encoding nucleotide sequences and said second set of allelic mutants comprises at least one donor pool of mutant encoding nucleotide sequences;

b) cloning each recipient pool of mutant encoding nucleotide sequences into a recipient vector;

c) transforming or transducing the recipient vector into a host cell to generate a pool of recipient cells;

d) cloning each donor pool of mutant encoding nucleotide sequences into a donor vector selected from the group consisting of phagemids and cosmids;

e) transforming or transducing the donor vector into a host cell to generate a pool of donor cells;

f) infecting the pool of donor cells with a helper phage to generate a mixture of donor phage particles, wherein said mixture comprises donor phage particles which contain said helper phage genome and phage particles which contain donor vectors having a mutant encoding nucleotide sequence;

g) clonally amplifying the pools of donor phage and recipient cells;

h) transducing the recipient cells with the mixture of donor phage particles to generate a set of recombinants; and i) screening the recombinants.

In a second embodiment, the invention is directed to a population of multiple protein variants prepared by the method disclosed herein.

These and other embodiments of the subject invention will readily occur to those of ordinary skill in the art in view of the disclosure herein.

DETAILED DESCRIPTION

Figure 1:
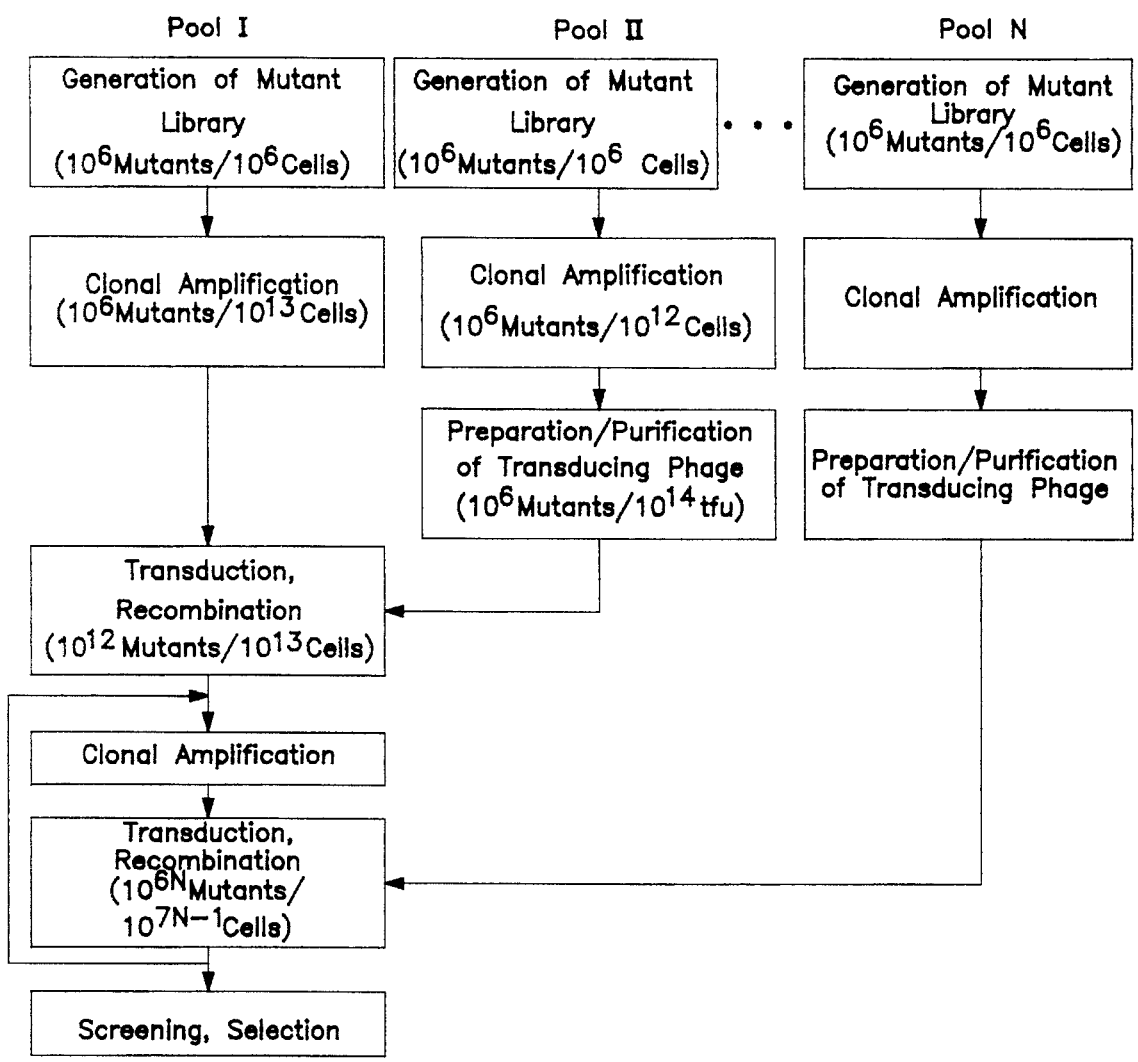
FIG. 1 depicts a general scheme for the generation of large numbers of multiple allelic mutants according to the present invention.

The practice of the present invention will employ, unless otherwise indicated, conventional techniques of molecular biology, microbiology and recombinant DNA technology, which are within the skill of the art. Such techniques are explained fully in the literature. See, e.g., Sambrook, Fritsch & Maniatis, Molecular Cloning: *A Laboratory Manual,* Second Edition (1989); *DNA Cloning, Vols. I and II* (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); the series, *Methods In Enzymology* (S. Colowick and N. Kaplan eds., Academic Press, Inc.).

All patents, patent applications and publications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

The terms "mutant" or "mutant encoding nucleotide sequence" are used interchangeably herein to indicate an oligonucleotide sequence which differs from a wild-type nucleotide sequence at one ("single mutant"), two ("double mutant"), three ("triple mutant") or more nucleotides. Such a mutant encoding nucleotide sequence is expressed as a protein "variant" which, as used herein, indicates a polypeptide sequence which may differ from that of the wild-type polypeptide and may or may not display a phenotypic difference in structure or function from the wild-type polypeptide.

By "amplification" or "clonal amplification" is meant a process whereby the density of host cells into which a population of mutant encoding nucleotide sequences has been cloned, or otherwise inserted, is increased. In other words, a pool of clones, or individual clones, which carry mutants are grown such that the relative number of independent mutants is not changed. As exemplified in FIG. 1, a population of $10^6$ mutants in $10^6$ cells, when amplified, results in a population of $10^6$ mutants in a $10^{12}$ cells.

As used herein, the term "cloning" is intended to encompass all methods by which DNA is transferred from a source organism, inserted into a cloning vector and then introduced into a host organism, e.g., *E. coli,* by methods which include transformation, in the case where a plasmid vector is used, transduction, when the vector is bacteriophage-based, and transfection, as referring to the uptake of foreign DNA by eukaryotic cells and its subsequent incorporation into the host cellular genome. In transduction, genetic material of one bacterial organism is transferred to another by a bacteriophage.

The terms "pool" of mutants, "mutant library" or "combinatorial library" are used interchangeably herein to indicate an ensemble of cloned random mutant encoding nucleotide sequences. A "pool" or "library" includes clones not only of mutant but also wild-type encoding nucleotide sequences. A "recipient" cell is a host organism transformed with a first mutant library into which the mutant library of a "donor" pool is transduced.

An "intermediate population" of cells harboring mutant encoding nucleotide sequences is a pool of such cells which, according to the design of a particular experimental protocol, is not the ultimately desired population of cells having the desired number of mutant encoding nucleotide sequences. Thus, as exemplified in FIG. 1, recipient cells transduced with cloned donor pools I, II, etc., to pool n-1, represent intermediate populations of recombinants.

"Recombination" is the naturally occurring, random reassortment of sections of DNA sequences between two DNA molecules. Such recombination can occur between DNA double helices, or between single stranded DNA and duplex DNA, via the formation of a heteroduplex complex. Recombination as used herein is a spontaneously occurring event following transduction of a recipient cell with a cloned donor pool. A "recombinant cell" or "recombinant" is used herein to indicate a cell which is the result of naturally occurring recombinational events. The mechanisms and frequency of occurrence of recombination are discussed further below.

By "screening" is meant a process whereby a population of mutant clones, transductants or recombinants is surveyed to determine whether there exists within this population one or more clones, transductants or recombinants which express a protein variant with the desired phenotype. After a population of mutant clones, transductants or recombinants has been screened and the expression of a desired phenotype within the population is confirmed, the clone, transductant or recombinant which express the desired phenotype may be "selected" from the population, by which is meant a process whereby the desired clone or clones may be identified to facilitate separation thereof from the general population of clones, transductants or recombinants.

The terms "polypeptide" and "protein" are used interchangeably and refer to any polymer of amino acids (dipeptide or greater) linked through peptide bonds. Thus, the terms "polypeptide" and "protein" include oligopeptides, protein fragments, analogs, muteins, fusion proteins and the like.

B. General Methods

Recombination-enhanced mutagenesis: FIG. 1 depicts a generalized protocol of the present invention for generating a combinatorial library, or pool, of allelic mutants. The numbers of mutants, cells, or phages present at each step in the protocol are calculated based upon typical efficiencies of standard mutagenesis and phage production techniques, as well as an estimate of the in vivo frequency of recombination (f) from the data in Table 1.

As summarized in FIG. 1, the methods of the present invention employ two or more pools of, for example, $10^6$ mutants each of the wild-type encoding nucleotide sequence. These mutants are generated using any convenient mutagenesis technique, described more fully below, and are inserted into cloning vectors.

More particularly, the wild-type encoding nucleotide sequence of a protein of interest may be obtained by a variety of techniques. For example, genomic and cDNA libraries, derived from a desired tissue, can be prepared using techniques well known in the art. Oligonucleotide probes which contain the codons for a portion of the known or determined sequence of the protein of interest can be prepared and used to screen the libraries for these nucleotide sequences. The basic strategies for preparing oligonucleotide probes and DNA libraries, as well as their screening by nucleic acid hybridization, are well known to those of ordinary skill in the art. See, e.g., *DNA Cloning:* Vol. I, supra; *Nucleic Acid Hybridization,* supra; *Oligonucleotide Synthesis,* supra; Sambrook et al., supra. Once a clone from the screened library has been identified by positive hybridization, it can be confirmed by restriction enzyme analysis and DNA sequencing that the particular library insert indeed contains a nucleotide sequence which encodes the desired protein and the nucleotide sequence can be isolated. See, e.g., Sambrook et al., supra.

If desired, the wild-type encoding nucleotide sequence can be prepared synthetically using techniques known in the art. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Random mutagenesis of the nucleotide sequences obtained as described above can be accomplished by several different techniques known in the art, such as by altering sequences within restriction endonuclease sites, inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants or by damaging plasmid DNA in vitro with chemicals. Chemical mutagens include, for example, sodium bisulfite, nitrous acid, hydroxylamine, agents which damage or remove bases thereby preventing normal base-pairing such as hydrazine or formic acid, analogues of nucleotide precursors such as nitrosoguanidine, 5-bromouracil, 2-aminopurine, or acridine intercalating agents such as proflavine, acriflavine, quinacrine, and the like. Generally, plasmid DNA or DNA fragments are treated with chemicals, transformed into *E. coli* and propagated as a pool or library of mutant plasmids.

Once the mutant sequences are generated, the DNA is inserted into an appropriate cloning vector, using techniques well known in the art (see, e.g., Sambrook et al., supra). The choice of vector depends on the pool of mutant sequences, i.e., donor or recipient, with which they are to be employed. Furthermore, the choice of vector determines the host cell to be employed in subsequent steps of the claimed method. Any transducible cloning vector can be used as a cloning vector for the donor pool of mutants. It is preferred, however, that phagemids, cosmids, or similar cloning vectors be used for cloning the donor pool of mutant encoding nucleotide sequences into the host cell. Phagemids and cosmids, for example, are advantageous vectors due to the ability to insert and stably propagate therein larger fragments of DNA than in M13 phage and λ phage, respectively. Phagemids which will find use in the present methods generally include hybrids between plasmids and filamentous phage cloning vehicles. Cosmids which will find use in the claimed methods generally include λ phage-based vectors into which cos sites have been inserted. Recipient pool cloning vectors can be any suitable plasmid. The cloning vectors into which pools of mutants are inserted may be identical or may be constructed to harbor and express different genetic markers (see, e.g., Sambrook et al., supra). The utility of employing such vectors having different marker genes may be exploited to facilitate a determination of successful transduction.

In one preferred embodiment, the cloning vector employed is a phagemid and the host cell is *E. coli*. Upon infection of the host cell which contains a phagemid, single-stranded phagemid DNA is produced, packaged and extruded from the cell in the form of a transducing phage in a manner similar to other phage vectors. Thus, clonal amplification of mutant encoding nucleotide sequences carried by phagemids is accomplished by propagating the phagemids in a suitable host cell.

Following clonal amplification, the cloned donor pool of mutants (pool II in FIG. 1) is infected with a helper phage to obtain a mixture of phage particles containing either the helper phage genome or phagemids mutant alleles of the wild-type encoding nucleotide sequence.

Infection, or transfection, of host cells with helper phage is generally accomplished by methods well known in the art (see, e.g., Sambrook et al., supra; and Russell et al. (1986) *Gene* 45:333–338).

The helper phage which find utility in the claimed methods may be any phage which can be used in combination with the cloning phage to produce an infective transducing phage. For example, if the cloning vector is a cosmid, the helper phage will necessarily be a λ phage. In one preferred embodiment, the cloning vector is a phagemid and the helper phage is a filamentous phage, and preferably phage M13.

If desired after infecting the phagemid with helper phage and obtaining a mixture of phage particles, the transducing phage can be separated from helper phage based on size differences (Barnes et al. (1983) *Methods Enzymol.* 101:98–122), or other similarly effective technique.

The entire spectrum of cloned donor mutations can now be transduced into clonally amplified recipient cells into which has been transduced or transformed a pool of mutant encoding nucleotide sequences. Recipient cells which may be employed in the method disclosed and claimed herein may be, for example, *E. coli*, or other bacterial expression systems which are not recombination deficient. A recombination deficient cell is a cell in which recombinatorial events is greatly reduced, such as the rec⁻ mutants of *E. coli* (see, Clark et al. (1965) *Proc. Natl. Acad. Sci.* USA 53:451–459).

Methods for transforming mutant encoding nucleotide sequences into recipient host cells are known to those of skill in the art and typically include the use of $CaCl_2$ or other agents, such as divalent cations and DMSO. DNA can also be introduced into bacterial cells by electroporation.

By maintaining a high multiplicity of infection (MOI) and a ratio of [transductant forming units (tfu)]: [plaque forming units (pfu)] greater than 1, one can ensure that virtually every recipient cell receives at least one mutant gene from the donor pool. The MOI is adjusted by manipulating the ratio of transducing particles to cell density. By the term "high multiplicity of infection" is meant a multiplicity of infection of greater than 1, preferably between 1 to 100, more preferably between 1 and 10.

It is preferred that the tfu:pfu ratio, as reflecting the ratio of transducing phages to helper phages, be as large as possible, at least greater than one, more preferably greater than 100 or more. By exercising the option to separate transducing phage from helper phage, as described above, the tfu:pfu ratio can be maximized.

These transductants can now be selected for the desired expressed protein property or characteristic and, if necessary or desirable, amplified. Optionally, if the phagemids into which each pool of mutants is cloned are constructed to express different genetic markers, as described above, transductants may be selected by way of their expression of both donor and recipient plasmid markers.

The recombinants generated by the above-described methods can then be subjected to selection or screening by any appropriate method depending on the sought after characteristic or property of the protein of interest, for example, enzymatic or other biological activity, binding to a receptor molecule, inhibition of the binding of another receptor ligand, or the like.

The above cycle of amplification, infection, transduction, and recombination may be repeated any number of times using additional donor pools cloned on phagemids, as depicted in FIG. 1. As above, the phagemids into which each pool of mutants is cloned may be constructed to express a different marker gene. Each cycle could increase the number of distinct mutants by up to a factor of $10^6$. Thus, if the probability of occurrence of an inter-allelic recombination event in any individual cell is f (a parameter that is actually a function of the distance between the recombining mutations), the transduced culture from two pools of $10^6$ allelic mutants will express up to $10^{12}$ distinct mutants in a population of $10^{12}/f$ cells.

Alternatively, by incorporating appropriate screening and/or selection steps on intermediate populations, multiple mutants can be isolated in which the mutated residues contribute non-additively to the relevant free energy parameter associated with protein function. For example, by subjecting pools I and II to negative selection prior to transduction, followed by imposition of positive selection on the recombinants, one can isolate many independent compensatory mutants (pseudorevertants). Characterization of such double mutants can provide invaluable information on structure-function relationships in the protein of interest.

Mechanisms and frequency of recombination: The mechanisms for interplasmidic recombination have been extensively studied (Clark et al. (1988) In: *The Recombination of Genetic Material*, Low (ed.), Academic Press, pp. 155–214). For example, using pBR322-based plasmids, recombination frequencies of $10^{-4}$–$10^{-3}$ have been reported between mutations separated by approximately 300 bp (Laban et al. (1981) *Molec. Gen. Genet.* 184:200–207).

Evidence from plasmid-phage systems suggests that f increases proportionately with increasing plasmid copy number (Watt et al. (1985) *Proc. Natl. Acad. Sci. USA* 82:4768–4772). In the method disclosed herein for generating variant proteins, the optimal value of f should be as high as possible. Thus, for the construction of phagemids, the use of very high copy number vectors, such as pUC vectors (Vieira et al. (1987) *Methods Enzymol.* 153:3–11), is preferred. Furthermore, since recombination in *E. coli* involves the homologous alignment of single stranded DNA with duplex DNA to produce a nascent heteroduplex structure (Weinstock (1987) In: *Escherichia coli and Salmonella typhimurium*, Niedhardt (ed.) American Society for Microbiology, pp. 1034–1043), the use of an M13-based transducing system has a preferred effect on the value of f. This has been shown to occur in bacterial suicide delivery systems for chromosomal gene disruption (Hillemann et al. (1991) *Nucleic Acids Res.* 19:727–731). With regard to the dependence of f on the length of homology between recombining mutations, a systematic study demonstrated that, while f varies exponentially at distances less than or equal to 53 bp (i.e., approximately 18 amino acids), it is only a weak function of the length of homology at distances of 74 bp or larger (i.e., more than 24 amino acids) (Watt et al., supra). Thus, the key to efficient sampling of multiple mutants appears to lie in the development of a protocol that (i) achieves the highest possible value of f for a given distance between mutations, and (ii) scales linearly (or better) with increasing volume.

The recombination frequency can be increased through the use of *E. coli* strains with specific allelic backgrounds. For example, the presence of certain sbcA or sbcB alleles in an *E. coli* host lead to interplasmid recombination frequencies that are higher than those observed in otherwise identical control strains (Laban et al., supra). More significantly, since the results of $10^7$–$10^8$ recombinants/mL are based upon the use of recipient cultures with comparatively low cell densities ($10^8$–$10^9$ cells/mL), considerable gains can be made through the use of higher cell densities ($10^{10}$–$10^{11}$ cells/mL) (Khosla et al. (1990) *Bio/Technology* 8:554–558).

Usages and advantages of the claimed invention: The methods disclosed and claimed herein find utility in a wide range of problems in protein science and engineering. For example, in phenomena as diverse as recognition, catalysis, transport and assembly, protein specificity is primarily due to the ability of a protein to accurately position multiple functional groups so as to facilitate non-covalent interaction with a target molecule. Since individual contributions of many of these functional groups are often marginal, the methods disclosed herein may be used to effectively search protein sequence space for subsets of relevant functional groups.

For example, the present invention finds particular utility in the engineering of antibodies. A typical heavy chain ($V_H$), which can be functionally expressed in *E. coli*, is made up of three complementarity determining regions (CDRs) of 4–9 amino acids each, separated by relatively invariant regions of 15–40 amino acids. Thus, starting with three CDR libraries, each containing approximately $10^6$ mutants in a particular CDR, a pool of *E. coli* cells expressing all $10^{18}$ combinations within the antigen binding site could be generated. This number exceeds the repertoire of naturally occurring immune systems by several orders of magnitude.

To exemplify its effectiveness, the method disclosed and claimed herein has been successfully applied to the problem of reverting two independent multiple mutants of mouse dihydrofolate reductase back to wild-type activity.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Experimental Materials and Methods

Bacterial strains and phages: $F^+$ *E. coli* strains, XL1-Blue (recA1, endA1, gyrA96, thi-1, hsdR17, supE44, relA1, lac, [F' proAB, lacI$^q$Z$\Delta$M15, Tn10 (tet$^r$)]; Stratagene) and L60 (HfrPO2A, $\Delta$(bet-lac), rel-1, tonA22, T2$^r$, Rif$^r$; (Styrvoid et al. (1986) *J. Bacteriol.* 165:856–863)), were used as hosts for donor and recipient phagemids, respectively, whereas phage R408 (Stratagene) was used as the M13 helper phage. The choice of XL1-Blue as the donor strain is based upon its ability to yield phage stocks that have two desirable properties: high tfu ($>10^{10}$ tfu/mL) and a high tfu/pfu ratio ($>1$). However, since XL1-Blue contains a null mutation in recA, which results in a strong block in interplasmidic recombination (Clark et al., supra), a recombination-proficient $F^+$ strain (L60) with a comparable transformation frequency to XL1-Blue was chosen as the recipient strain for these studies.

Culture conditions and phage methods: Standard conditions for cell growth as well as preparation of helper and transducing phage were used (Sambrook et al. (1989) Molecular Cloning: A *Laboratory Manual*, Cold Spring Harbor Laboratory Press, pp. 4:21–4:23). To increase the yield of transductants per ml culture volume, phage prepared from donor cells was infected into stationary-phase recipient cells.

EXAMPLE 1

Construction of Donor and Recipient Phagemids

Figure 2A:
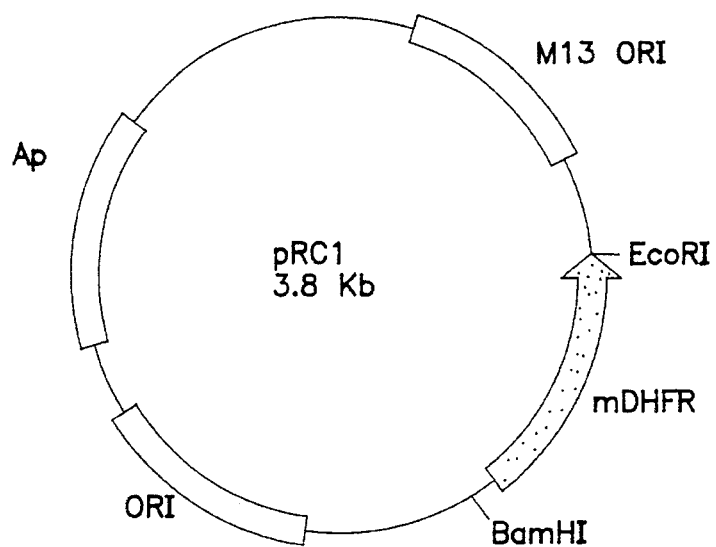
FIG. 2A and FIG. 2B are diagrams of phagemids pRC1 and pRC2, respectively.
Figure 2B:
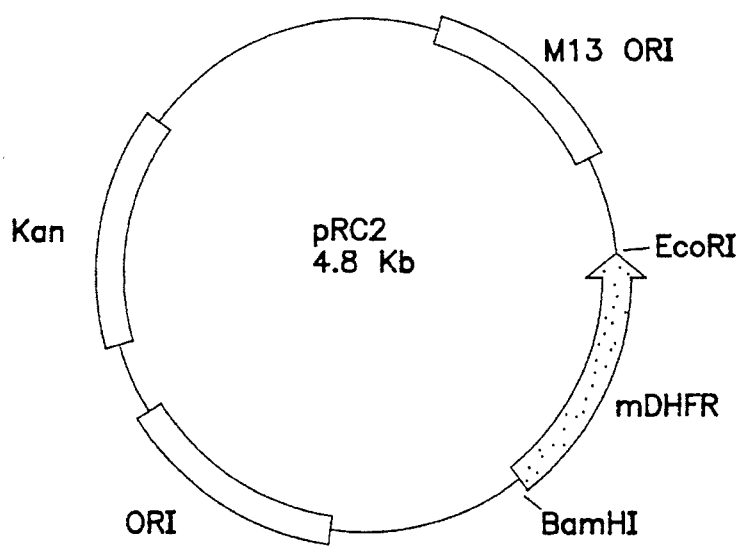

The donor and recipient phagemids used in this Example are shown in FIGS. 2A and 2B, respectively. Each is a derivative of pUC119 (Vieira et al., supra). A BamHI/EcoRI fragment carrying the mDHFR gene together with a synthetic ribosome binding site was cloned into pUC119 to yield the donor phagemid pRC1. The recipient phagemid, pRC2, was identical to pRC1, except for replacement of the AatII/ScaI fragment (which includes most of the Ap gene) with a 1.5 kb end-filled SalI fragment (Pharmacia) containing the Kan gene from Tn903. Two crossovers must occur for a mutation on pRC1 to recombine with one on pRC2 (or vice versa). Since more than 1 kb homology is available on either side of the mDHFR gene, the crossover event between the two mutations is likely to limit the recombination frequencies observed.

EXAMPLE 2

Construction of mDHFR Mutants

The mDHFR gene possesses a unique SstI site at position 256 in the reading frame. Two additional unique restriction sites, BspEI and EagI, were engineered at positions 81 and 195 respectively. Each of the three sites were individually blunted to yield three frameshift mutants, mut1, mut2, and mut3, shown in FIGS. 3A, 3B and 3C, respectively. In addition, two mDHFR multiple mutants, mut4 and mut5, were constructed using successive rounds of error-prone PCR mutagenesis (Leung et al. (1989) *Technique* 1:11–15), and cloned into pRC1. From the first round of mutagenesis a trimethoprim-sensitive mutant, containing 7 missense mutations and a spontaneous reversion frequency of approximately $10^{-6}$, was isolated. With this mutant as a template, a second round of PCR mutagenesis yielded two mutants, mut4 and mut5, with a total of 13 and 14 missense mutations, respectively. Both mut4 and mut5 had undetectable ($<10^{-12}$) frequencies of spontaneous reversion, implying that at very least, two mutation events needed to occur in each case in order to revert them back to trimethoprim resistance.

EXAMPLE 3

Transduction Efficacy and Recombination Frequency

Figure 3A:
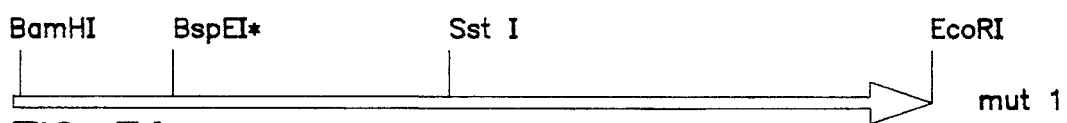
FIG. 3A, 3B and 3C depict frameshift mDHFR mutants mut1, mut2, and mut3, respectively. In each case the * represents the position of the frameshift.
Figure 3B:
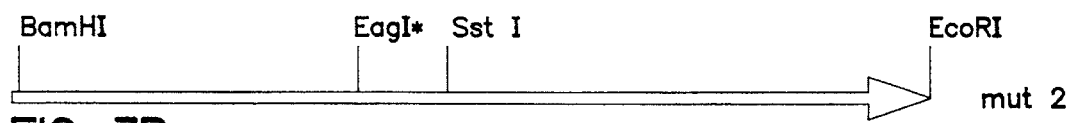
Figure 3C:
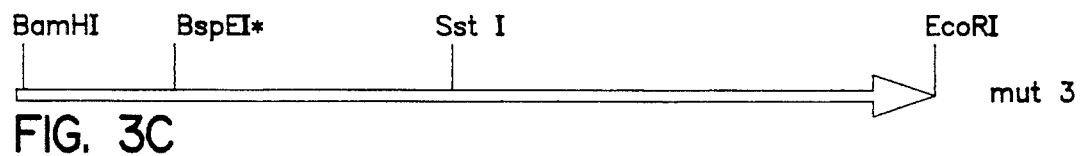

In order to characterize the efficacy of the transduction of recipient cells with cloned donor pools of mutants and the frequency of recombination which occurs thereafter, a set of mutants, mut1, mut2, and mut3, in the gene encoding mDHFR, was constructed as described in Example 2. mut1, mut2, and mut3, depicted in FIGS. 3A, 3B and 3C, respectively, are null mutants constructed by introducing frameshifts at naturally occurring or genetically engineered restriction sites. These mutations occur at 86 bp (29 amino acids), 200 bp (67 amino acids), and 257 bp (86 amino acids) into the mDHFR reading frame. mut1 and mut3 were cloned into both the donor and the recipient phagemid (pRC1 and pRC2, respectively), whereas mut2 was only cloned into pRC1. These mutants were used to measure in vivo recombination frequencies.

The results of recombination experiments between these mutations are summarized in Table 1. From these data, the following conclusions can be drawn: (i) virtually every recipient cell can be transduced with at least one (or more) donor mutants; (ii) mutations separated by as little as 19 amino acids can recombine at greater than 1% frequency; (iii) a maximum

TABLE 1

Measurement of Transduction and Recombination Frequencies[a]

| Donor | Recipient | Culture Volume[b] | Total Cell Density (A) (Kan$^r$) ($10^9$ cells/ml) | Transductant Cell Density (B)[c] (Kan$^r$ Carb$^r$) ($10^9$ cells/ml) | Recombinant Cell Density (C) (Tp$^r$) ($10^7$ cells/ml) | Transduction Efficiency (B/A) Kan$^r$ Carb$^r$ / Kan$^r$ | Apparent Recombination Frequency[d] (C/B) Tp$^r$ / Carb$^r$ Kan$^r$ |
|---|---|---|---|---|---|---|---|
| mut 1 | mut 1 | 2 ml | 1.1 ± 0.5 | 1.2 ± 0.2 | <0.005 | 1.1 ± 0.5 | <10$^{-4}$ |
| mut 3 | mut 3 | 2 ml | 1.3 ± 0.1 | 0.5 ± 0.1 | <0.005 | 0.4 ± 0.1 | <10$^{-4}$ |
| mut 3 | mut 1 | 2 ml | 1.0 ± 0.1 | 0.9 ± 0.6 | 4.3 ± 3.6 | 0.9 ± 0.6 | 0.04 ± 0.02 |
| mut 2 | mut 1 | 2 ml | 1.1 ± 0.1 | 0.9 ± 0.3 | 7.0 ± 4.7 | 0.8 ± 0.3 | 0.08 ± 0.03 |
| mut 2 | mut 3 | 2 ml | 1.5 ± 0.2 | 1.1 ± 0.1 | 1.3 ± 0.5 | 0.8 ± 0.2 | 0.02 ± 0.01 |
| mut 2 | mut 1 | 50 ml | 1.3 ± 0.1 | 1.3 ± 0.1 | 11.3 ± 0.7 | 1.0 ± 0.1 | 0.09 ± 0.01 |

[a]Averaged data from two or three independent experiments.
[b]2 ml experiments were conducted in culture tubes, whereas 50 ml experiments were conducted in baffled shake flasks.
[c]To ensure that the transductants and recombinants obtained in these experiments are truly independent (i.e., they do not include transductants/recombinants obtained from subsequent rounds of phage biosynthesis and release), the above counts were obtained from cells plated out approximately 1 hour after adding phage. This was estimated to be the minimum length of time required for infection by transducing phage, recombinations, and expression of trimethoprim resistance.
[d]For the experiments involving crosses between mut 1 and mut 3 candidate colonies were examined by restriction mapping to confirm the predicted structure of the recombinant.

(distance-independent) apparent recombination frequency of 5–10% is observed for mutants separated by more than 38 amino acids; (iv) using the method described here, one can reproducibly sample up to $10^8$ independent recombinants per mL culture (this number may have been even higher due to the high MOI used); and (v) since the method scales linearly with volume, and is amenable to even further improvement using high-cell density fermentation techniques, a 100 L fermentation could be expected to contain as many as $10^{15}$ genetically distinct mutants. In other words, by combining this method with cassette mutagenesis (Cormack et al., supra), one can express all possible triple mutants of mDHFR in which the mutations are separated by 20 or more amino acids.

EXAMPLE 4

Application of Recombination-enhanced Mutagenesis to One-step Isolation of Desirable Multiple Mutants To evaluate the applicability of recombination-enhanced mutagenesis to combinatorial problems in protein engineering, two multiple mutants of mDHFR (mut4 and mut5) were constructed using two rounds of error-prone PCR mutagenesis. Cells expressing Mut4 or Mut5 are sensitive to trimethoprim, and do not revert back to trimethoprim resistance at detectable frequencies. It has been estimated that at least two mutation events are needed in order to revert mut4 or mut5 back to trimethoprim resistance. Using error-prone PCR mutagenesis with mut4 and mut5 as templates, two mutant libraries were constructed in pRC1, and transformed into XL1-Blue. $10^5$ independent mutants were obtained in each case. The same libraries were also introduced into L60 by transformation. No trimethoprim-resistant colony could be isolated from either library in either host. However, by subjecting these mutant libraries to the procedure outlined in FIG. 1 under conditions similar to those described in Table 1, at least one trimethoprim-resistant clone was found in each case. (Since these revertants were isolated from 50 ml cultures grown overnight in the presence of trimethoprim, the exact number of truly independent revertants could not be determined.) In a control experiment, where unmutagenized mut4 and mut5 were used as donors, no revertants were isolated. Based on measurements of the apparent recombination frequency, it is estimated that the diversity of the mutated DHFR library constructed using recombination-enhanced mutagenesis is on the of the order $10^{10}$ independent mutants. The presence of at least one revertant in each recombined pool supports this conclusion.

Thus, a novel method of generating multiple protein variants has been disclosed. Although preferred embodiments of the subject invention have been described in some detail, it is to be understood that obvious variations can be made without departing from the spirit and the scope of the invention as defined by the appended claims.

We claim:

1. A method of generating multiple protein variants, wherein said method comprises:
   a) providing first and second sets of allelic mutants, wherein said first set of allelic mutants comprises at least one recipient pool of mutant encoding nucleotide sequences and said second set of allelic mutants comprises at least one donor pool of mutant encoding nucleotide sequences;
   b) cloning each recipient pool of mutant encoding nucleotide sequences into a recipient vector;
   c) transforming or transducing the recipient vector into a host cell to generate a pool of recipient cells;
   d) cloning each donor pool of mutant encoding nucleotide sequences into a donor vector selected from the group consisting of phagemids and cosmids;
   e) transforming or transducing the donor vector into a host cell to generate a pool of donor cells;
   f) infecting the pool of donor cells with a helper phage to generate a mixture of donor phage particles, wherein said mixture comprises donor phage particles which contain said helper phage genome and phage particles which contain donor vectors having a mutant encoding nucleotide sequence;
   g) clonally amplifying the pools of donor phage and recipient cells; and
   h) transducing the recipient cells with the mixture of donor phage particles to generate a set of recombinants;
   i) screening the recombinants.

2. The method of claim 1, wherein the donor vector is a phagemid.

3. The method of claim 2, wherein the host cell is a bacterium.

4. The method of claim 3, wherein the bacterium is *Escherichia coli*.

5. The method of claim 2, further comprising separating phage particles which contain a helper phage genome from phage particles which contain a phagemid having a mutant encoding nucleotide sequence.

6. The method of claim 5, wherein the phage particles which contain a helper phage genome are separated from the phage particles which contain a phagemid by size difference.

7. The method of claim 2, further comprising maintaining a multiplicity of infection of at least one and a transductant-forming-unit to plaque-forming-unit ratio (tfu/pfu) of at least one.

8. The method of claim 2, wherein each recipient vector expresses a distinct genetic marker.

9. The method of claim 2, further comprising repeating steps (c) to (i) using additional cloned donor pools of mutant encoding nucleotide sequences.

10. The method of claim 2, wherein each phagemid expresses a distinct genetic marker.

11. The method of claim 2, wherein the helper phage is a filamentous phage.

12. The method of claim 11, wherein the filamentous phage is M13.

13. The method of claim 1, further comprising screening intermediate populations.

14. A population of multiple protein variants prepared by a process comprising the steps of:
   a) providing first and second sets of allelic mutants, wherein said first set of allelic mutants comprises at least one recipient pool of mutant encoding nucleotide sequences and said second set of allelic mutants comprises at least one donor pool of mutant encoding nucleotide sequences;
   b) cloning each recipient pool of mutant encoding nucleotide sequences into a recipient vector;
   c) transforming or transducing the recipient vector into a host cell to generate a pool of recipient cells;
   d) cloning each donor pool of mutant encoding nucleotide sequences into a donor vector selected from the group consisting of phagemids and cosmids;
   e) transforming or transducing the donor vector into a host cell to generate a pool of donor cells;
   f) infecting the pool of donor cells with a helper phage to generate a mixture of donor phage particles, wherein said mixture comprises donor phage particles which contain said helper phage genome and phage particles which contain donor vectors having a mutant encoding nucleotide sequence;

g) clonally amplifying the pools of donor phage and recipient cells;

h) transducing the recipient cells with the mixture of donor phage particles to generate a set of recombinants; and i) screening the recombinants.

15. The population of claim 14, prepared by the process wherein the donor vector is a phagemid.

16. The population of claim 15, prepared by the process wherein the host cell is a bacterium.

17. The population of claim 16, prepared by the process wherein the bacterium is *Escherichia coli*.

18. The population of claim 15, prepared by the process further comprising separating phage particles which contain a helper phage genome from phage particles which contain a phagemid having a mutant encoding nucleotide sequence.

19. The population of claim 18, prepared by the process wherein the phage particles which contain a helper phage genome are separated from the phage particles which contain a phagemid by size difference.

20. The population of claim 15, prepared by the process further comprising maintaining a multiplicity of infection of at least one and a transductant-forming-unit to plaque-forming-unit ratio (tfu/pfu) of at least one.

21. The population of claim 15, prepared by the process wherein each recipient vector expresses a distinct genetic marker.

22. The population of claim 15, prepared by the process further comprising repeating steps (c) to (i) using additional cloned donor pools of mutant encoding nucleotide sequences.

23. The population of claim 15, prepared by the process wherein each phagemid expresses a distinct genetic marker.

24. The population of claim 15, prepared by the process wherein the helper phage is a filamentous phage.

25. The population of claim 24, prepared by the process wherein the filamentous phage is M13.

26. The population of claim 15, wherein the process further comprises screening intermediate populations.

* * * * *